(12) United States Patent
Feierabend et al.

(10) Patent No.: US 7,659,993 B2
(45) Date of Patent: Feb. 9, 2010

(54) METHOD AND DEVICE FOR WAVE-FRONT SENSING

(75) Inventors: Marcus Feierabend, Heidelberg (DE); Markus Rückel, Heidelberg (DE); Winfried Denk, Heidelberg (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 136 days.

(21) Appl. No.: 11/200,457

(22) Filed: Aug. 9, 2005

(65) Prior Publication Data

US 2006/0033933 A1 Feb. 16, 2006

(30) Foreign Application Priority Data

Aug. 11, 2004 (EP) .................................. 04019068

(51) Int. Cl.
*G01B 11/02* (2006.01)
(52) U.S. Cl. ........................................ 356/512; 356/497
(58) Field of Classification Search ................ 356/495, 356/511–515
See application file for complete search history.

(56) References Cited

U.S. PATENT DOCUMENTS

| | | | | |
|---|---|---|---|---|
| 5,489,984 | A * | 2/1996 | Hariharan et al. | 356/512 |
| 5,570,182 | A * | 10/1996 | Nathel et al. | 356/511 |
| 6,608,717 | B1 * | 8/2003 | Medford et al. | 359/368 |
| 6,649,895 | B1 * | 11/2003 | Wirth | 250/201.9 |
| 6,769,769 | B2 * | 8/2004 | Podoleanu et al. | 351/221 |
| 7,168,807 | B2 * | 1/2007 | Chernyak et al. | 351/246 |
| 2002/0033947 | A1 * | 3/2002 | Grunwald et al. | 356/450 |
| 2004/0061830 | A1 * | 4/2004 | Hellmuth et al. | 351/205 |
| 2004/0196450 | A1 * | 10/2004 | Levecq et al. | 356/121 |
| 2006/0058682 | A1 * | 3/2006 | Miller et al. | 600/476 |

OTHER PUBLICATIONS

Albert et al., "Smart microscope: an adaptive optics learning system for aberration correction in multiphoton confocal microscopy", Optics Letters, vol. 25 (1), pp. 52-54 (2000).*
Merkle et al., "Successful Tests of Adaptive Optics", ESO Messenger, vol. 58, pp. 1-4 (1989).
Platt et al., "Lenticular Hartmann Screen", Optical Sciences Center Newsletter, vol. 5, p. 15 (1971).

(Continued)

*Primary Examiner*—Tarifur Chowdhury
*Assistant Examiner*—Jonathan M Hansen
(74) *Attorney, Agent, or Firm*—Caesar, Rivise, Bernstein Cohen & Pokotilow, Ltd.

(57) ABSTRACT

A method for sensing a wave-front of specimen light scattered from an illuminated area in a specimen (10) includes the steps of focusing illumination light into the specimen (10), directing specimen light scattered in the specimen (10) to a detector device (50) having a plurality of detector elements (51) and being capable to sense light with local resolution, detecting sample light contained in the specimen light with the detector device (50), said sample light being scattered in a predetermined sample plane (11) of the specimen (10) and being selected by a time-based gating of the specimen light, locally resolved measuring phase information of the sample light, and reconstructing the wave-front of the sample light on the basis of the phase information. Furthermore, a method of microscopic imaging with adapted illumination light is described.

27 Claims, 4 Drawing Sheets

OTHER PUBLICATIONS

Bille et al., "Imaging of the Retina by Scanning Laser Tomography", SPIE, vol. 1161, pp. 417-425 (1989).

Liang et al., "Supernormal vision and high-resolution retinal imaging through adaptive optics", J. Opt. Soc. Am. A., vol. 14 (11), pp. 2884-2892 (1997).

Sherman et al., "Adaptive correction of depth-induced aberrations in multiphoton scanning microscopy using a deformable mirror", Journal of Microscopy, vol. 206, pp. 65-71 (2002).

Marsh et al., "Practical implementation of adaptive optics in multiphoton microscopy", Optics Express, vol. 11 (10), pp. 1123-1130 (2003).

Neil et al., "Adaptive aberration correction in a two-photon microscope", Journal of Microscopy, vol. 200, pp. 105-108 (2000).

Cubalchini, "Modal wave-front estimation from phase derivative measurements", J. Opt. Soc. Am., vol. 69, pp. 972-977 (1979).

Malacara, "Optical Shop Testing" in "Wiley Series in Pure and Applied Optics", John Wiley & Sons, Inc., New York, $2^{nd}$ Ed., pp. 510-513 (1992).

Carré, Installation et utilisation du comparateu photoélectrique et interférentiel du Bureau International des Poids et Mesures, Metrologia, vol. 2, pp. 13-23 (1966).

Crane, Chapter V., "Interference Phase Measurement", Applied Optics, vol. 8, pp. 538-542 (1969).

Miller et al., "Coherence Gating and Adaptive Optics in the Eye", SPIE, vol. 4956, pp. 65-72 (2003).

Ash et al., "Optimal Hartmann sensing at low light levels", Optics Communications, vol. 156, pp. 10-15 (1998).

Roggemann et al., "Comparison of Fourier phase spectrum estimation using deconvolution from wavefront sensing and bispectrum reconstruction", Optics Communications, vol. 133, pp. 381-392 (1997).

* cited by examiner

METHOD AND DEVICE FOR WAVE-FRONT SENSING

SUBJECT OF THE INVENTION

The present invention relates to methods and devices for sensing the wave-front of light scattered in a specimen. Furthermore, the invention relates to methods and devices for imaging a specimen, in particular to microscopy methods and devices using illumination light with an adapted wave-front.

BACKGROUND OF THE INVENTION

An important goal of in-vivo microscopy is diffraction limited imaging from layers deep within biological specimens. In practice, diffraction limited resolution is often not achievable due to distortions of the wave-front introduced by refractive index inhomogeneities in the specimen.

An analogue problem is present in astronomy where wave-front distortions may be caused by refractive index variations due to turbulences in the atmosphere. These distortions are routinely corrected using adaptive optics (see F. Merkle et al. "Successful Tests of Adaptive Optics" in "ESO messenger", vol. 58, 1989, pages 1-4). Adaptive wave-front correction can be obtained by determining the distortion e.g. with the help of a bright star or an artificial reference such as a "laser guide-star". The wave-front distortion is directly measured by subjecting light from the reference star e.g. to a Shack-Hartmann wave-front sensor (B. Platt et al. "Lenticular Hartmann Screen" in "Optical Sciences Center Newsletter", vol. 5, 1971, p. 15). In the Shack-Hartmann wave-front sensor, the wave-front to be measured is directed to a regular array of microlenses. In the focal plane of these lenses, a CCD camera detects the light distribution of all lenses passed by the wave-front. The wave-front is reconstructed numerically from this distribution of light portions.

In microscopy, the adaptation technique known from infrared astronomy generally cannot be applied since neither natural nor artificial "guide stars" are available in a specimen like e.g. a biological specimen. The only situation where wave-front measuring techniques from astronomy can be directly applied is when the light comes primarily from the focal plane. This is the case in the eye, where a single tissue layer (the retina) reflects or backscatters most of the light, which can than be used to determine the distortion caused by lens and cornea (see J. F. Bille et al. "Imaging of retina by scanning laser tomography" in "Proc. SPIE", vol. 1161, 1989, p. 417-425; J. Z. Liang et al. "Supernormal vision and high-resolution retina imaging through adapted optics" in "J. Opt. Soc. Am. A", vol. 14 (11), 1997, p. 2884-2892).

Generally, biological or synthetical specimens have an inhomogeneous structure with different refractive indices in different structures. As an example, in a biological specimen a blood vessel may lie between a focal region of interest and a surface of the specimen causing an essential distortion of the light to be detected. For these less favourable biological specimens, wave-front measuring techniques from astronomy cannot be directly applied. Therefore, techniques have been proposed, which use the fact that one has considerable control of and information about the wave-front of the light source (e.g. scanning laser) for illuminating the specimen.

One conventional approach for wave-front correction in multiphoton or confocal microscopy is an iterative wave-front optimization using a search algorithm based on trial distortions of the incident wave-front. As an example, O. Albert et al. ("Smart microscope: an adaptive optics learning system for aberration correction in multi-photon confocal microscopy" in "Optics Letters", vol. 25, 2000, p. 52-54) propose 5 an illumination of the specimen with a computer-controlled deformable mirror in conjunction with a learning algorithm to compensate for the static off axis aberrations. This approach uses the fact that the amount of fluorescence generated in the focal plane of the specimen strongly depends on the quality of the focus. Similar iterative wave-front optimization procedures are described by L. Sherman et al. ("Adaptive correction of death induced aberrations in multi-photon scanning microscopy using a deformable mirror" in "Journal of Microscopy", vol. 206, 2002, p. 65-71), and P. M. Marsh et al. ("Practical implementation of adaptive optics in multi-photon microscopy" in "Optics Express", vol. 11, 2003, p. 1123-1130).

These trial-and-error approaches can be used in thick, scattering samples such as e.g. brain tissue. However, these conventional procedures have the following disadvantages. Generally, the conventional procedures allow indirect measurements only. This means, that detecting of any wave-front distortion requires an illumination with a deformed illumination wavefront. Secondly, the iterative wave-front optimization requires the presence of a sufficiently bright fluorescence signal. Therefore, samples with sensitive fluorophores cannot be investigated due to photo bleaching. Furthermore, the iterative optimization is only feasible if the search space is sufficiently low dimensional, which limits the order to which distortion can be corrected. A further disadvantages is related to the high time consumption of the search algorithm using the deformable mirror.

M. A. A. Neil et al. ("Adaptive aberration correction in a two-photon-microscope" in "Journal of Microscopy", vol. 200, 2000, p. 105-108) have proposed a direct measurement of the wave-front by evaluating the fluorescence emission of a specimen. The fluorescence measurement represents an essential disadvantage with regard to the investigation of sensitive samples.

OBJECT OF THE INVENTION

The object of the invention is to provide improved methods and devices for sensing a wave-front of light scattered from a specimen in an imaging device, e.g. in a microscope, said methods and devices overcoming the disadvantages of the conventional techniques and having an extended range of applications, in particular for the investigation of strongly scattering samples and samples which are sensitive to photo bleaching. A particular object of the invention is the provision of a wave-front sensing method and device allowing an improved correction of optical errors, in particular specimen-induced aberrations in microscopy. Furthermore, the object of the invention includes the provision of improved imaging methods and devices.

SUMMARY OF THE INVENTION

This object is solved by methods and devices of the invention.

According to a first general aspect of the present invention, the wave-front of light influenced in particular by a transmission through a specimen is determined by the evaluation of coherence-gated light scattered in a predetermined sample plane of interest.

In response to a focussed illumination of the specimen, light is scattered from the entire illumination cone, in particular both from a focal plane of illumination as well as from out-of-focus areas. In the following, the scattered light is generally called specimen light. According to the present invention, only a predetermined portion of the specimen light scattered in the predetermined sample plane is detected with a detector device having a two-dimensional detector area. This light portion (in the following: sample light) is selected by a time-based gating (coherence gating) of the specimen light. The detection of the sample light comprises a light detection during a restricted time range corresponding to the arrival of light scattered in the sample plane of interest. The specimen influences the phase information of the light scattered in the specimen. Accordingly, refractive index inhomogeneities in the specimen can be determined by reconstructing the wave-front of the detected sample light. The sample light detection allows a discrimination against backscattered light coming from layers above or below the plane of interest.

Essential advantages of the invention are represented by the fact that the wave-front of the sample light is sensed on the basis of a direct measurement of phase information of scattered light. The method of the invention allows the provision of a quantitative representation of the wave-front. Furthermore, the method of invention allows a separation of wave-front sensing and a further investigation (e.g. imaging) of the specimen. Generally, the wave-front can be determined from scattered sample light without an excitation of fluorescence. Accordingly, the coherence-gated wave-front sensing method of the invention is applicable in particular to specimens that are only weakly or sparsely fluorescent, or to specimens that are photosensitive or easily bleached.

Generally, the time-based gating of specimen light can be implemented with all techniques allowing a discrimination on time-scale with sufficient response time. According to a preferred embodiment of the invention, the selective detection of sample light is obtained by an interferometric superposition of the specimen light with reference light having a predetermined time-relationship relative to the illumination light. The interferometric superposition of specimen and reference light has an essential advantage with regard to the deletion of out-of-plane light with a coherence length being determined by the spectral distribution of the light source only. Alternative methods of time-based gating of the specimen light can be implemented with conventional non-linear optical gates based e.g. on the Kerr effect.

Preferably, pulsed-shaped illumination light is split into light pulses directed to the specimen and reference light pulses. The optical path length of at least one of the sample and reference light paths can be adjusted such that the arrival time of an illumination light pulse scattered from the sample plane of interest on the detector device is identical with the arrival time of a corresponding reference light pulse. Interference of sample and reference light pulses is occurring only within the coherence length of the light pulses. Accordingly, the detector device detects light portions formed by this time-gated interference only.

As a result of the interference of sample and reference light, the sample wave-front is measured relative to the wave-front of the reference light. If the reference light has a plane wave-front (which is usually the case in particular with the setup described below), the sample wave-front is directly measured as such.

As the detectable light intensity of the superimposed sample and reference light contains the phase information of the sample light scattered in the predetermined sample plane, this phase information can be obtained with local resolution directly from measuring the light intensities at the detector elements of the detector device. According to this embodiment of the invention, the phase function (wave-front) is directly derived from the superimposed light intensities measured at each of the detector elements. According to an alternative embodiment, sub-groups of detector elements are considered each corresponding to a sub-aperture of the detector device. In this case, the phase function is directly derived from the superimposed light intensities measured at each of the sub-groups of detector elements. This procedure may have an advantage of averaging wave-front structures which are caused by speckle rather than by the influence of the inhomogeneities in the specimen.

According to a further preferred embodiment, the intensities measured at the sub-groups of detector elements are subjected to an operation simulating the imaging function which would be performed by a Shack-Hartmann-Sensor in a plane of each sub-group. Accordingly, the complex phase of the sample light derived from the intensity distribution detected with each sub-group of detector elements is subjected to a Fourier transformation corresponding to the imaging function of a lens of a real Shack-Hartmann-Array.

The implementation of the Shack-Hartmann-Sensor simulation has the following advantages. Firstly, evaluation algorithms developed for real Shack-Hartmann wave-front sensors are available. These algorithms can be applied directly in particular for measuring the directional derivative of the phase (see R. Cubalchini "Modal wave-front estimation from phase derivative measurements" in "Journal of the Optical Society of America", vol. 69, 1979, p. 972-977). A further substantial advantage of the wave-front sensor simulation compared to real wave-front sensors is a much larger effective dynamic range of detection because light intensity at the detector plane is relatively uniform, so that pixel saturation is avoided. Furthermore, the virtual sensor allows a software-based modification (election) of the size of the above sub-groups. Depending on the specimen, the size can be increased so that the processing speed is increased, or the size can be decreased so that the local resolution is increased. Another advantage of the virtual Shack-Hartmann-Array is the elimination of any optical errors which could be introduced by real lenses.

According to an alternative embodiment of the invention, the phase information can be obtained from light intensity distributions determined with a real wave-front sensor, in particular with a Shack-Hartmann-Array of lenses. The provision of a real optical component may represent advantages with regard to the processing speed.

In accordance with a further embodiment of the invention, an optical path length modulation may be introduced in at least one of the sample and reference light paths so that the step of selectively detecting sample light can be repeated with various relative path length differences of sample and reference light. This embodiment of the invention results in essential advantages for a quick and precise algorithm-based reconstruction of the wave-front. Preferably, the wave-front of the sample light is calculated on the basis of at least three path length differences. For the implementation of a four-step PSI-algorithm (see D. Malacara "Optical shop testing" in: "Wiley Series in Pure and Applied Optics", John Wiley & Sons, Inc., New York, 1992, 2nd ed.), path lengths differences according to 0, $\lambda/4$, $\lambda/2$ and $3\lambda/4$ are preferred, with $\lambda$ representing the centre wavelength of the illumination light.

Generally, the wave-front is represented by a two-dimensional function. According to a preferred embodiment of the invention, the wave-front, i.e. this two-dimensional function is reconstructed on the basis of an approximation by a mathematically complete set of functions, in particular on the basis of a set of orthogonal polynomials.

Particularly preferred is the approximation by sum of Zernike polynomials. Generally, Zernike polynomials are a convenient set of circular basis functions which may be used to represent the phase distribution over the aperture of the imaging system in a mathematical form. A sum of a number of polynomials, each with its own weighting, may be used to reconstruct the degraded wave-front. Zernike polynomials are used as a preferred type of polynomials as they have a close correspondence with the different types of aberrations occurring in the imaging system.

The coherence gating of sample light according to the present invention can be used to select a predetermined sample plane in the depth of the specimen. This ability of free selection represents an essential advantage compared with the conventional techniques. According to a particularly preferred embodiment of the invention, the selected sample plane is even the focal plane of the specimen, i.e. the plane, into which the illumination light is focussed with a focussing optic. In this case, the sample light scattered from the focal volume in the illumination cone can be evaluated with the method of the invention. The focal point or focal volume represents a point-like light source being restricted to a volume of some picolitres. The wave-front distortion sensed according to the invention essentially is introduced into the sample light coming from this light source when the light pulse travels back through the specimen and to the detector device.

According to a second general aspect of the invention, the above object is solved by a microscopy method for imaging a specimen, wherein the illumination light for microscopy (in the following: adapted illumination light) is provided with a wave-front adaptation compensating for wave-front distortions introduced by the specimen. The adapted illumination light is generated with an adapted (or: corrected) wave-front formed on the basis of a so called sensed wave-front which has been obtained with a method according to the above first aspect of the invention. The adapted wave-front is generated with a wave-front corrector device arranged in the illumination light path.

The essential advantage of the present microscopy method is given by the fact that the adapted illumination wave-front is deformed during the passage through the specimen such that a diffraction limited focal point can be obtained. Extensions or deformations of the focal point which would be obtained without the wave-front adaptation are avoided. In contrast to the conventional iterative procedures of wave-front correction, the microscopy method of the present invention is characterized by a high detection speed. Any genetic wave-front deformation algorithm can be avoided.

A further preferred embodiment of the invention allows an accelerated image collection by sensing the wave-front at a sub-group of pixels rather then at each sample pixel to be imaged. According to the invention, it is not strictly necessary to sense the sensed wave-front at the same location like the focal point of interest for the microscopic imaging. Instead, the sensed wave-front may be sensed at a neighbouring point without a lost of quality in the focal point of the adaptive illumination light. In particular, an averaged sensed wave-front sensed at a predetermined focal point of the specimen can be used for providing the adapted illumination wave-front for illuminating a plurality of focal points surrounding this predetermined point used for wave-front sensing. The use of an averaged sensed wave-front essentially increases the speed of recording images of the focal plane.

Wave-front corrector devices are available as such e.g. from astronomy. According to a preferred embodiment of the invention, a deformable mirror or a liquid crystal spatial light modulator is used as the wave-front corrector device. Deformable mirrors are preferably used in view of their short response time. On the other hand, the adjustment of a liquid crystal spatial light modulator being usable in a transmission or reflection mode has advantages with regard to the precision of wave-front adaptation.

Preferably, the present imaging method is implemented as a fluorescence microscopy method, i.e. fluorescence is excited with the adapted illumination light at the respective focal points. The combination of wave-front sensing of back-scattered light with the image sampling on the basis of fluorescence light represents an essential advantage of the present invention. The wave-front sensing can be implemented with a low illumination intensity which does not bleach the specimen. Another important advantage is obtained as the fluorescence can be linearly excited as in the conventional confocal microscopy, or non-linearly exited as in the conventional multi-photon excitation microscopy. Accordingly, the invention can be combined without problem with available fluorescence microscopy methods.

According to a third general aspect of the invention, a wavefront sensing device is provided with an optical splitting device being arranged for splitting illumination light into a sample light path for focussed illumination and detection of specimen light as well as into a reference light path for forming a time-gate for sample light from a predetermined sample plane. Furthermore, the wave-front sensing device of the invention comprises a detector device with two-dimensional sensitivity and an evaluation device being connected with the detector device for reconstructing the wave-front of the sample light detected. The provision of the reference light path is advantageous in terms of time-based or coherence-based filtering of the specimen light allowing a direct measurement of the wave-front as outlined above. In contrast to conventional optical setups, the device of the present invention directly provides a quantitative representation of the wave-front.

Preferably, the illumination light is provided with a laser light source (pulse laser) generating laser pulses.

According to a preferred embodiment of the invention, at least one of the sample and reference light paths has an adjustable optical path length advantageously allowing the selection of the sample plane in the specimen.

Preferably, the sample and reference light paths form an interferometer being arranged for a superposition of the reference light and the specimen light at the detector device. Alternatively, the reference light path may be used for directing a switching light pulse to a light shutter being operated on the basis of the Kerr effect.

According to a fourth general aspect of the invention, an imaging device (microscope) for microscopic imaging a specimen is proposed which comprises the wave-front sensing device according to the invention as well as a wave-front corrector device arranged in the sample light pulse.

BRIEF DESCRIPTION OF THE DRAWINGS

Further details and advantages of the invention will be described in the following with reference to preferred embodiments being illustrated in the attached drawings. In the drawings.

DETAILED DESCRIPTION OF PREFERRED EMBODIMENTS OF THE INVENTION

1. Optical Setup of a Wave-Front Sensing Device

Figure 1:
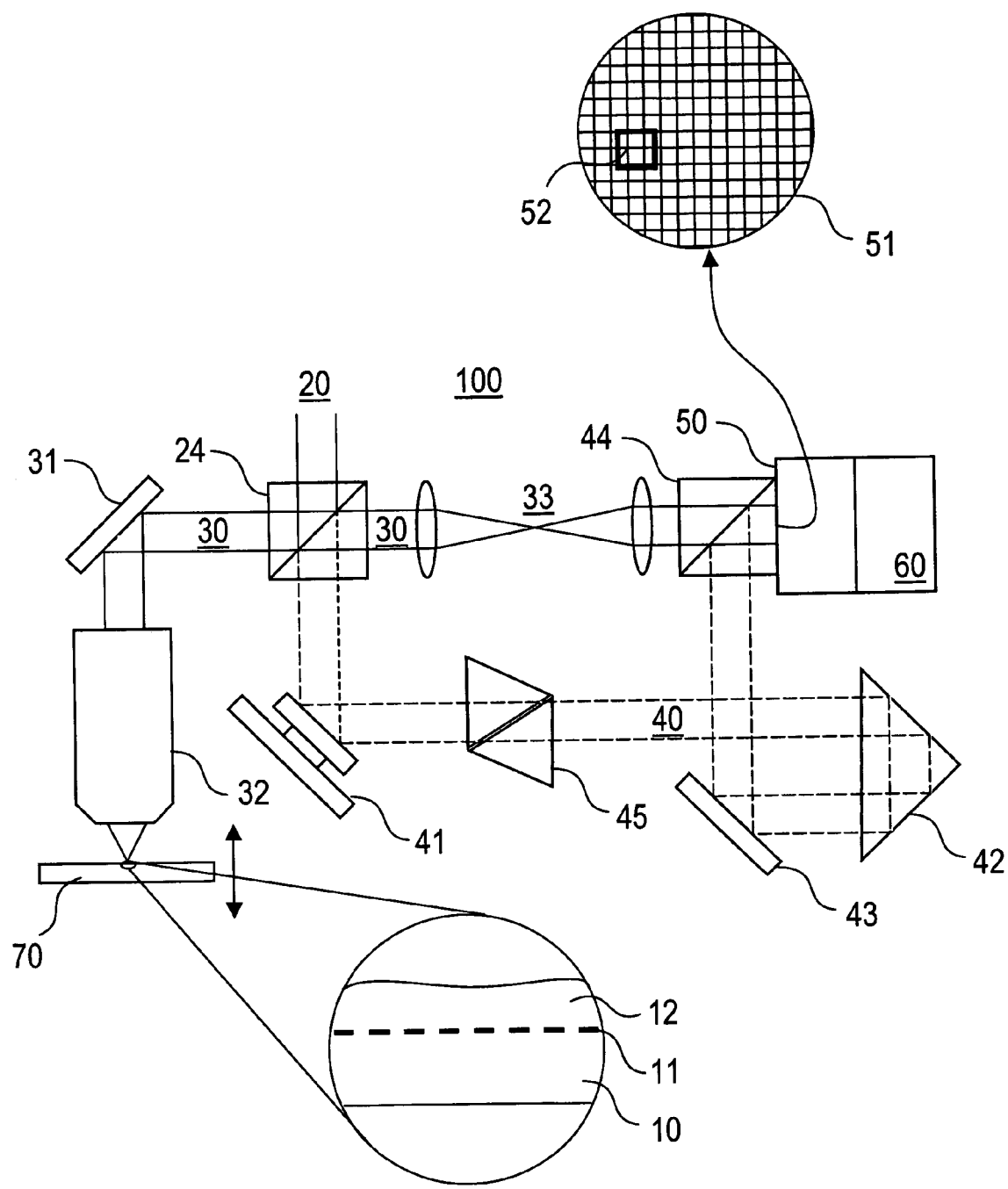
FIG. 1: is a schematic illustration of an embodiment of a wave-front sensing device according to the invention.

According to the embodiment illustrated in FIG. 1, the wave-front sensing device 100 of the present invention comprises an illumination light path 20, which is split at the beam splitter cube 24 into the sample light path 30 and the reference light path 40.

Figure 3:
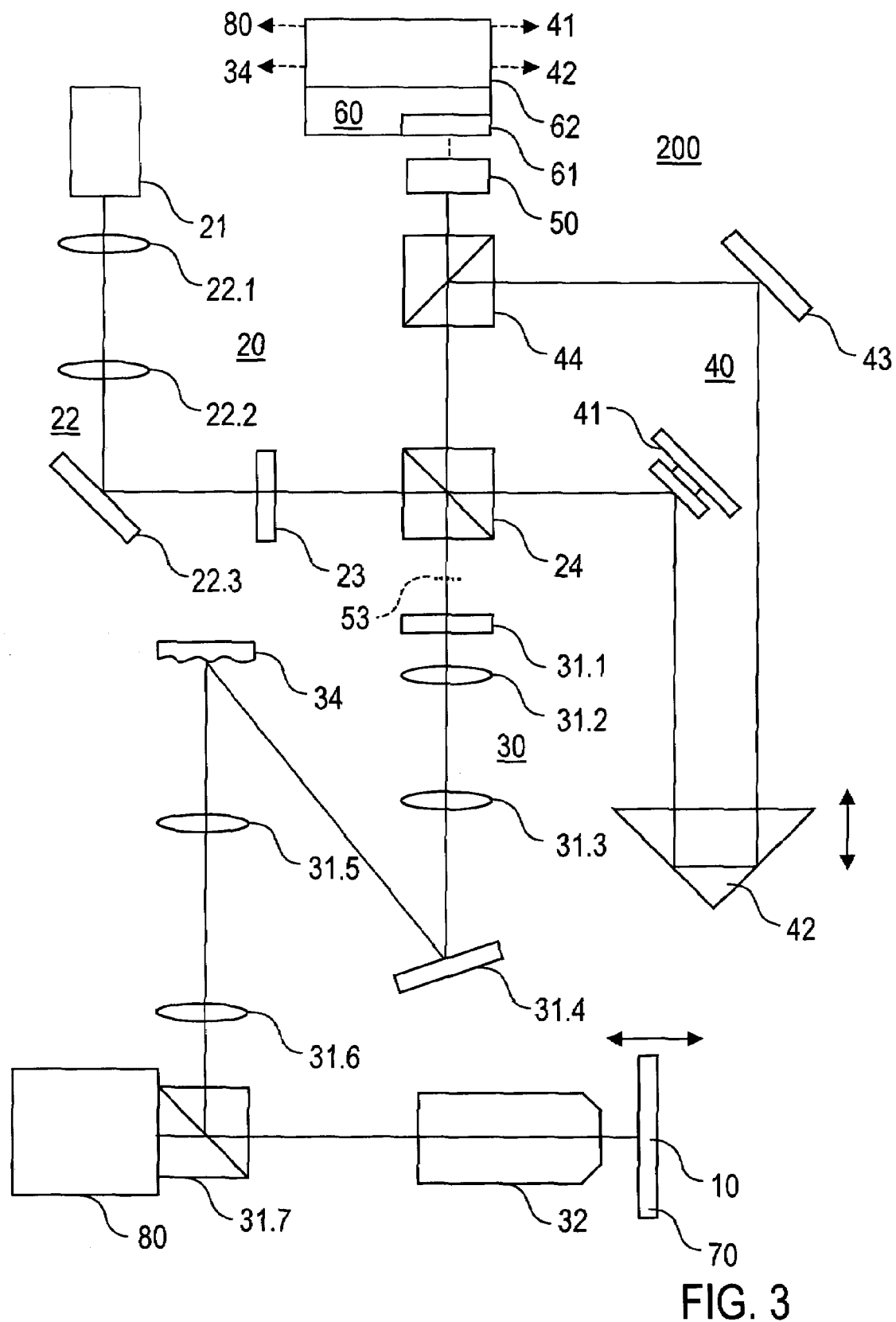
FIG. 3: is a schematic illustration of an embodiment of the imaging device according to the invention.

The illumination light path 20 includes a laser light source and optical components, which are shown with further details in FIG. 3. The laser light source is a Ti:sapphire laser (Coherent Mira, centre wavelength 915 nm) emitting horizontally polarized light pulses with a pulse duration of about 100 fs. The beam splitter cube 24 is a non-polarizing 50:50 splitter (BK 7, Coherent, Inc.).

The sample light path 30 extends from the beam splitter cube 24 via a deflection mirror 31 and a focussing optic 32 to the specimen 10 and in opposite direction from the specimen 10 via the focussing optic 32, the mirror 31, the beam splitter cube 24, an imaging optic 33 and a beam splitter cube 44 to the detector device 50. The deflection mirror 31 is a plane mirror (protected silver, Linos), the focussing optic 32 is a microscope objective (Zeiss IR-Acroplan 63 x/0.90W). The imaging optic 33 comprises two lenses (Linos, NIR-doublets f=140 mm) which image the back focal plane of the focussing optic 32 onto the detector elements 51 of the detector device. The detector elements 51 are formed by a CCD-Chip (Sony XC-77, pixel dimension about 13 µm·13 µm). Groups of detector elements 51 represent so called sub-groups 52 to be used for the virtual wave-front sensor (see below). A sub-group 52 of detector elements comprises e.g. 15*15 detector elements 51.

The specimen 10 is positioned with a specimen holding device 70 in the optical axis of the focussing optic 32. As the specimen holding device 70, any sample carrier or sample table for microscopy can be used which is capable to be shifted at least in a direction parallel to the optical axis of the focussing optic 32 (see double arrow). The expanded sectional view of the specimen 10 (bottom of FIG. 1) illustrates schematically the irregular shape of the specimen 10 into which the illumination light is focussed to the focal plane 11. Out-of-focus regions 12 in the upper illumination cone of the specimen 10 influence the wave-front of the light travelling through these regions.

The reference light path 40 extends from the beam splitter cube 24 via a modulator mirror 41, a set of matching prisms 45, a deflection prism 42, a deflection mirror 43 and the beam splitter cube 44 to the detector device 50. The modulator mirror 41 comprises a plane mirror (protected silver, Linos) mounted on a piezo actuator (PCL 100-40, Linos). The matching prisms 45 comprise 4 glass dispersion matching prisms (60°, BK 7, equilateral prisms, Linos), while the deflection prism 42 is a single right angle prism (BK 7, Linos) for 180° deflection. Mirror 43 is a plain mirror (protected silver, Linos). The beam splitter cube 44 is a non-polarizing cube (BK 7, Linos).

The deflection prism 42 is arranged for calibrating the reference path length with regard to the selected sample plane in the specimen to be investigated. For this calibration, a reflecting mirror can be positioned in the specimen holding device 70 instead of the specimen.

The detector device 50 is connected with an evaluation device 60. The evaluation device 60 contains a processor portion for reconstructing the wave-front of the sample light on the basis of the phase information obtained from the detector device. Further details of the evaluation device 60 are described with reference to FIG. 3.

2. Wave-Front Sensing

The wave-front sensing device 100 represents a low coherence interferometer with the focussing optic 32 and the specimen 10 in the sample arm (path 30) and the path length-varying modulator mirror 41 in the reference arm (path 40). Coherence gating is achieved by phase-shifting interferometry (PSI), which is described e.g. by P. Carre "Installation et Utilisation du comperateur photonelectrique et interferentiel du Bureau International des Poids et Mesures" in "Metrologia", vol. 2, 1966, p. 13-23, and by R. Crane, Chapter V. "Interference phase measurement" in "Applied Optics", vol. 8, 1969, p. 538-542.

The PSI procedure both rejects wrong path-length light and extracts the phase and thus the wave-front information from the sample light scattered in the focal plane 11 of the specimen 10. The interference signal falls of rapidly with arm length mismatch, which leads to a selection volume of about 6 pl and a depth discrimination of about 30 µm in the focal plane 11. These dimensions represent examples only which are determined by the coherence length of the laser light source. The extracted phase can be used to calculate the complex field amplitude in the plane of the detector elements 51.

In a preferred embodiment, a four-step PSI algorithm has been used where quadruplets of images (I1 ... I4) are taken with optical path length differences of 0, $\lambda/4$, $2\lambda/4$ and $3\lambda/4$, respectively. For each pixel, a complex amplitude (A) is calculated using the equation:

$$A = (I_1 - I_3) + i(I_4 - I_2) = 4\sqrt{I_{reference}I_{sample}} \, (\cos\Delta\phi + i \cdot \sin\Delta\phi)$$

with $\Delta\phi$ being the phase difference (path length difference) of the reference and sample light arms 40, 30.

For simulating a Shack-Hartmann sensor, the propagation of the complex amplitude through a virtual lenslet array was calculated. Each lens of this virtual array is assigned to a sub-group 52 of detector elements 51. From the light intensity measured at each detector element, the phase information and the above complex amplitude is obtained. The complex amplitudes of each sub-group 52 are subjected to a Fourier transformation simulating the optical imaging function of a corresponding lenslet. Phase slope extraction was obtained by fitting the peak position in the focal plane of the virtual lenslets and comparing them to the lenslet centers.

To validate the wave-front sensing of the invention, several tests were performed using a scattering phantom comprising 112 nm polystrene beads (Polysciences Inc.) as scatterers embedded in agarose (HMP 2%, Sigma Inc.) at a concentration of about $9.8 \times 10^{13}$ beads/ml. According to Mie theory the scattering anisotropy and scattering length are about 0.24 and about 400 µm, respectively. The phantom also contained 2.5 µm diameter fluorescence beads (Molecular Probes) at about $2.1 \times 10^7$ beads/ml, which were used to measure the mean free path with 2-photon microscopy. The focal plane of the focussing optic 32 was positioned approximately 1 mean free path (MFP) below the specimen surface. The fraction of the total light passing the coherence gate (CG) and thus being used for wave-front sensing was estimated to be about $1.3 \times 10^{-3}$, using that in the thickness of the coherence gate about 13.2% can be collected (given isotropic scattering) by the solid angle of the objective. In addition the attenuation of the incoming and outgoing light (about 63.2% each way) has been taken into account. For both scattering and attenuation the Lambert-Beer law was used.

According to the above equation, the fraction of the light ($I_{s\text{-}coh}/I_{s\text{-}total}$) in the sample arm that is coherent with the reference arm can be calculated using $I_{s\text{-}coh}/I_{s\text{-}total}=|A|^2/(16 \cdot I_{reference} \, I_{s\text{-}total})$. In the present case, this fraction was $(0.55\pm0.08)\times10^{-3}$, which is slightly lower than the "Lambert-Beer" value. The 'useful' light typically corresponds to $2\pm0.3$ photons per camera pixel and frame, which is considerably below the dark noise of 218 photons but can still be detected, owing to the interferometric detection.

(a) The first wave-front aberration artificially introduced to test the wave-front sensing was defocus. Since moving the sample up and down does not change the average backscattered wave-front the reference path length was changed to shift the CG position relative to the focus. For each CG position 600 image quadruplets were taken at 24 different sample positions (shifts of 0.1 µm) to reduce speckle noise. The peak shifts were determined and then averaged over sample positions for each virtual lenslet. Finally, the Zernike fit was performed.

Figure 2:
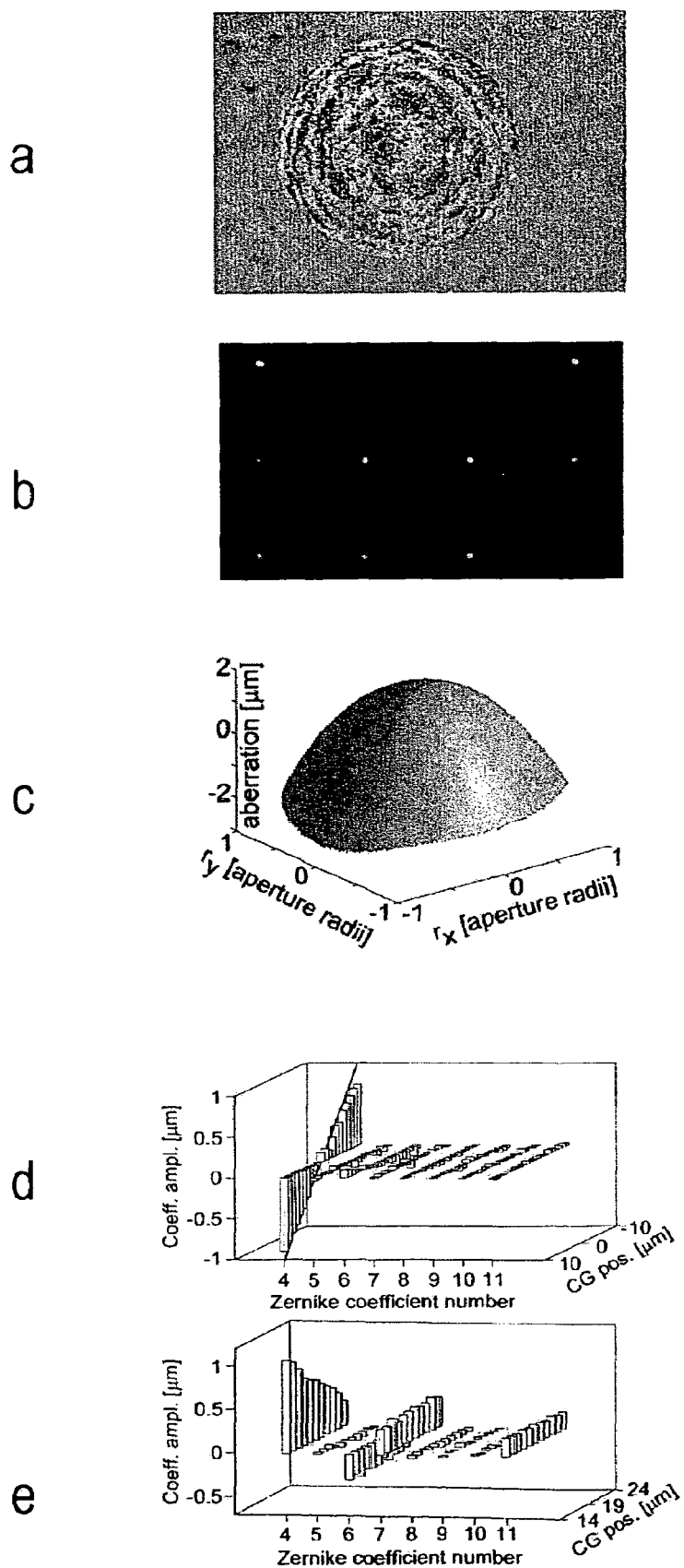
FIG. 2: illustrates experimental results obtained with the wave-front sensing device shown in FIG. 1.

FIG. 2a illustrates the real part of the complex wave-front amplitude in the whole aperture for a 10 µm defocus calculated using the above equation. The arrangement of virtual Shack-Hartmann-Spots generated by the above simulation (numerical propagation) are illustrated in FIG. 2b, wherein the magnified view of a small sub region is shown only. A corresponding example of a wave-front representation reconstructed using a modal estimation algorithm is shown in FIG. 2c.

FIG. 2d shows the Zernike coefficients (Z4-Z11) as a function of the position of the coherence gate. Negative positions represent a position of the coherence gate between the focal plane and the focussing optic 32. The solid line shows the theoretical expectation for defocus. The Zernike coefficient for defocus (Z4) is dominant and changes linearly with the CG position. The expected value for Z4 can be estimated by using that the optical path length difference between wave-front center and wave-front edge due to defocus is $\Delta z \cdot n \cdot (1-\cos\alpha)$, with $\Delta z$ the shift from the focus, n the refractive index, and $\alpha$ the edge-ray angle. The measured slope (dZ4/dz) is $-0.083\pm0.002$. All higher Zernike coefficients were small.

(b) Other aberrations were tested as well. The wave-front was distorted by inserting between objective lens and sample a glass cover slip (BK7, 180 µm thick; focal plane about 400 µm below the sample surface) with the surface normal tilted away from the optical axis (about 15°). In the Zernike fit strong astigmatism (Z6=(−0.26±0.03) µm, expected: Z6=−0.23 µm for a spherical wave emitted from the focus), coma (Z7=(0.33±0.03) µm), and spherical aberration (Z11 (0.2±0.01) µm) have been found. Unlike uniform curvature (Z4), which leads to a change of focus position but not shape, these aberrations do lead to a distortion of the focus and need to be corrected for optimal imaging. Finally, the effect of changing the CG position (from 14 µm to 24 µm below the original objective focus position in steps of 1 µm was tested); averaging was done as above but with sample position shifts of 0.5 µm). Only Z4 (defocus) changed systematically (slope: −0.073±0.003). FIG. 2e shows the Zernike coefficients (Z4-Z11) as a function of the position of the coherence gate with the tilted glass plane between the specimen and the focussing optic.

The illustrated results show that coherence gating of backscattered light can be used to measure wave-front distortions in scattering samples in the presence of background light that is dominant by about three orders of magnitude. The coherence gating technique according to the invention has the additional advantage of increasing the effective sensitivity, with potentially shot-noise limited performance even for low photon fluxes and detectors with large dark noise. This will allow the use of CMOS detector chips, which could in the future contain additional procession circuitry to perform the PSI and even the wave-front calculations on the chip. Detection sensitivity and processing speed will be central for the eventual implementation of closed loop adaptive optics systems for scattering samples.

3. Optical Setup of an Imaging Device

FIG. 3 illustrates an embodiment of an imaging device 200 according to the present invention. Basically, the imaging device (microscope 200) represents the optical setup as shown in FIG. 1 with the illumination light path 20, the sample light path 30 and the reference light path 40. The imaging device 200 is adapted for multiphoton microscopy, wherein the specimen scanning is obtained with a movement of the specimen holding device. The invention can be implemented correspondingly with a conventional confocal microscope. In this case, further known details like e.g. an optical scanning mechanism, a mechanical scanning mechanism and/or a pinhole diaphragm would be added.

The illumination light path 20 comprises the laser light source 21, beam forming elements 22 with a pair of imaging lenses 22.1, 22.2 and a deflection mirror 22.3, and a $\lambda/2$ plate 23 for controlling the intensity ratio in the sample and reference light paths 30, 40. At the beam splitter cube 24, the illumination light is split into the sample light path 30 and the reference light path 40. The beam splitter cube 24 is a polarizing cube. The provision of the polarizing beam splitter has the advantage of a high light efficiency. Any lost of light is avoided to the polarization selective splitting.

The sample light path extends from the beam splitter cube 24 via a $\lambda/4$ plate, beam forming elements 31.2 to 31.7, a deformable mirror 34 (OKO Technologies) and the objective 32 to the specimen 10. The beam forming elements comprise in particular two pairs of imaging lenses 31.2, 31.3 and 31.5, 31.6, a plane deflection mirror 31.4, and the dichroic beam splitter cube 31.7. The deformable mirror 34 is adapted to a predetermined shape in order to form the desired wave-front of the travelling light pulses. The objective 32 is the same like the focussing optic shown in FIG. 1. The specimen 10 is arranged on a movable specimen holding device 70. In the opposite direction, the sample light path 30 extends from the specimen 10 via the above mentioned optical components, the polarizing beam splitter cube 24 and the beam splitter cube 44 to the detector device 50, which is connected with the evaluation device 60. Fluorescence light emitted from the specimen 10 can be collected with a photomultiplier 80.

As shown in FIG. 1, the reference light path 40 comprises the modulator mirror 41, the deflection prism 42, the deflection mirror 43 and the beam spltter cube 44.

In FIG. 3, the evaluation device 60 is illustrated with further details. It contains a simulation circuit 61 being adapted for implementing the wave-front simulation algorithm, in particular the Shack-Hartmann algorithm described above. Furthermore, the evaluation device 60 contains a control circuit 62 which in particular is connected with the deformable mirror 34, the light sensing device 80 and the movable components 41, 42 in the reference light pulse 40.

If the wave-front sensing is obtained with a real array of lenses, e.g. the Shack-Hartmann-Array 53 is arranged in the sample light path 30 between the beam splitting cube 24 and the λ/4 plate 31.1 as shown with dotted lines.

4. Microscopic Imaging

Figure 4:
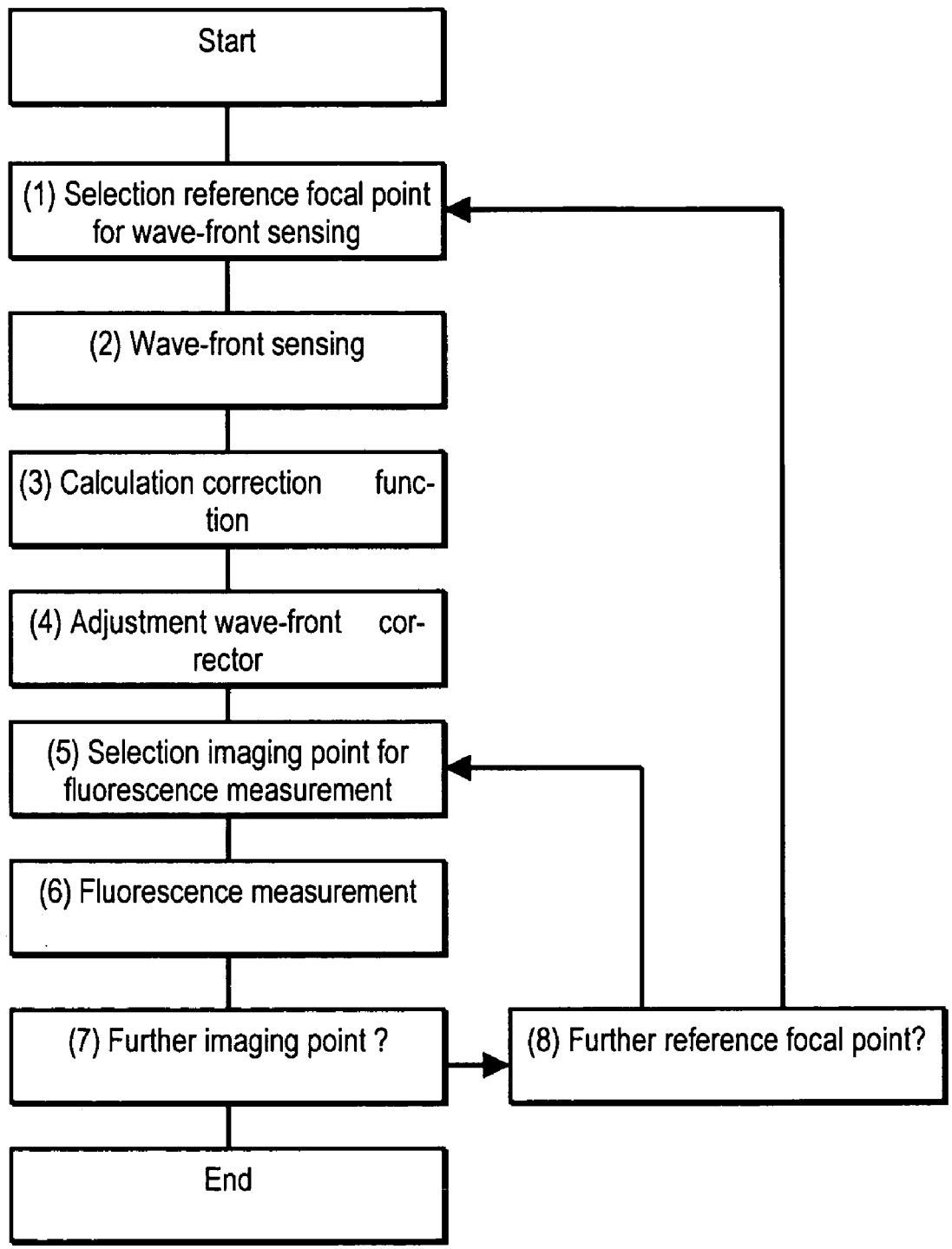
FIG. 4: is a flow diagram illustrating steps of an imaging method according to an embodiment of the invention.

FIG. 4 illustrates a preferred procedure for microscopic imaging a specimen using the wave-front sensing method according to the invention. After positioning the sample to be investigated on the specimen holding device 70 (see FIG. 3), a first focal point in the focal plane of the specimen is selected for wave-front sensing (step 1). To this end, the deflection prism 42 in the reference light path is adjusted such that the optical path length from the beam splitter cube 24 through the reference light path 40 to the beam splitter cube 44 is identical with the path length from the beam splitter cube 24 to the focal plane 11 in the specimen (see FIG. 1) and back to the beam splitter cube 44.

In the following, the wave-front sensing of the invention is performed (step 2). On the basis of the wave-front of sample light originating from the selected focal point, a correction function is calculated (step 3) with the control circuit 62 (see FIG. 3). The correction function represents a wave-front deformation phase-conjugated to the sensed wave-front. Subsequently, the wave-front corrector (mirror 34) is adjusted on the basis of the correction function (step 4).

In the following, the microscopic fluorescence measurement is conducted. At step 5, the first focal point is selected for the microscopic imaging. This first focal or imaging point (pixel) may be the first reference focal point selected for wave-front sensing or another focal point in the neighbourhood thereof. As the next step (step 6), the fluorescence measurement is performed by exciting the selected imaging point and collecting the fluorescence with the photomultiplier 80.

For taking a microscopic image of the specimen, a plurality of imaging points are detected. After the decision as to whether a further imaging point is to be detected (step 7), a further decision is made as to whether the illumination of the next imaging point is to be adapted with the wave-front obtained at the first reference focal point or not (step 8). This decision depends on the structure (homogeneity) of the specimen and the extension of the region of interest to be investigated. If a new reference focal point is to be selected, steps 1 to 4 are repeated. Otherwise, the next fluorescence measurement is performed (step 5).

5. Further Applications

In analogy to the above microscopy method, the present invention can be used for optimizing the focus in optical coherence tomography (high resolution back-scattering) and/or in retina imaging techniques, e.g. for measuring the thickness or any abnormal states in the retina of a human eye.

Furthermore, the focus for optical reading and/or writing can be improved on the basis of wave-front sensing and illumination adaptation according to the invention. This yields an improvement of optical data storage techniques in terms of storage density.

What is claimed is:

1. A method for sensing a wave-front of light totally back-scattered from an illuminated area in a specimen, said method comprising the steps of:

focusing illumination light from a laser light source via a focusing optic into the specimen;

directing the totally back-scattered light via an imaging optic to a detector device having a plurality of detector elements and sensing light with local resolution wherein said imaging optic images a back focal plane of the focusing optic onto the detector elements;

coherence-gating of the totally back-scattered light comprising an interferometric superposition of the totally back-scattered light with reference light split from the illumination light of the laser light source, wherein the reference light is directed through a reference light path from a beam splitting device to the detector elements of the detector device, the reference light path having an optical reference path length identical with an optical sample path length from the beam splitting device via a predetermined sample plane of the specimen to the detector device;

measuring the coherence-gated light intensities contained in the totally back-scattered light at each of the detector elements, said coherence-gated light intensities being scattered in the predetermined sample plane of the specimen and being selected by the coherence-gating of the totally back-scattered light;

locally resolved measuring phase information based on the coherence-gated light intensities, said phase information being influenced by light scattering in the specimen;

modulating at least one of the optical sample and reference path lengths and repeating the steps of selectively detecting coherence-gated light intensities and measuring phase information with various path length differences in the sample and reference paths set by said modulating; and reconstructing the wave-front of the coherence-gated light intensifies on the basis of the phase information obtained with the various path length differences.

2. The method according to claim 1, wherein the coherence-gated light intensities measured with sub-groups of the detector elements are subjected to a Shack-Hartmann-Sensor simulation resulting in sub-aperture images of the coherence-gated light, and the wave-front is obtained from the sub-aperture images.

3. The method according to claim 1, wherein the step of measuring the coherence-gate light intensities and the step of locally resolve measuring phase information comprise the steps of:

transforming the totally back-scattered light into a plurality of coherence-gated light portions by subjecting the totally back-scattered light to a wave-front sensor sampling a plurality of portions of the totally back-scattered light passing through an aperture of the detector device;

determining light intensity distributions of the coherence-gated light portions; and obtaining the phase information from the light intensity distributions.

4. The method according to claim 3, wherein the wave-front sensor comprises a Shack-Hartmann-Array of lenses.

5. The method according to claim 1, wherein the various path length differences comprise at least three values with an equidistant distribution within one light oscillation period.

6. The method according to claim 5, wherein the various path length differences comprise 0, λ/4, λ/2 and 3λ/4, wherein λ is the center wavelength of the illumination light.

7. The method according to claim 1, wherein the step of reconstructing the wave-front of the coherence-gated light comprises approximating the wave-front by a set of orthogonal polynomials.

8. The method according to claim 7, wherein the step of reconstructing the wave-front of the coherence-gated light comprises approximating the wave-front by a sum of Zernike polynomials.

9. The method according to claim 1, wherein the coherence-gated light is scattered in a focal plane of the specimen.

10. A method of microscopic imaging a specimen, said method comprising the steps of:

illuminating at least one focal point of the specimen with adapted illumination light having an adapted wave-front being formed with a wave-front corrector device phase-conjugated to a sensed wave-front obtained with a method according to claim 1, and detecting light emitted from the specimen in response to the adapted illumination light.

11. The microscopic imaging method according to claim 10, wherein the sensed wave-front is obtained at the at least one focal point or in a neighborhood of the at least one focal point.

12. The microscopic imaging method according to claim 10, wherein the illuminating and detecting steps are repeated at a plurality of focal points of the specimen.

13. The microscopic imaging method according to claim 12, wherein the adapted illumination wave-front at each of the focal points is formed phase-conjugated to an averaged sensed wave-front sensed at a neighboring point or in a neighborhood of the respective focal point.

14. The microscopic imaging method according to claim 10, wherein the wave-front corrector device comprises a deformable mirror or a liquid crystal spatial light modulator.

15. The microscopic imaging method according to claim 10, wherein the detecting step comprises sensing of fluorescence light emitted at the focal point.

16. The method according to claim 1, further comprising generating adapted illumination light having an adapted wave-front for optimizing a focus of illumination light in at least one of optical coherence tomography, retina imaging techniques, and optical reading or writing for optical data storage.

17. A wave-front sensing device for sensing a wave-front of light totally back-scattered from an illuminated area in a specimen, said wave-front sensing device comprising:

an optical splitting device arranged for focused introduction of illumination light via a focusing optic onto the specimen;

a detector device for detecting totally back-scattered light from the specimen, wherein the detector device comprises a plurality of detector elements for sensing light with local resolution, wherein an imaging optic is arranged between the optical splitting device and the detector device and said imaging optic images a back focal plane of the focusing optic onto the detector elements;

each of the detector elements of the detector device being arranged for obtaining an aberration measurement, wherein said aberration measurement contains both phase information and a complex amplitude of the totally back-scattered light with local resolution, said phase information being influenced by light scattering in the specimen; and a modulator, wherein:

a sample light path is formed between the optical splitting device and the detector device and the specimen is arranged in the sample light path, so that the totally back-scattered light can be directed via the imaging optic to the detector device;

a reference light path is formed for selecting coherence-gated light from the totally back-scattered light, said coherence-gated light being scattered in a predetermined sample plane of the specimen and said reference light path being split from the sample light path at the optical splitting device;

the modulator is arranged for modulating a phase relationship between the totally back-scattered light and reference light by modulating at least one of the optical sample and reference path lengths for obtaining various path length differences;

wherein said detector device further receives said coherence-gated light; and an evaluation device is provided which is connected with the detector device for reconstructing the wave-front of the coherence-gated light on the basis of phase information obtained with the various path length differences.

18. The wave-front sensing device according to claim 17, wherein at least one of said coherence-gated light path and said reference light path has an adjustable optical path length.

19. The wave-front sensing device according to claim 17, wherein the reference light path is formed for interferometric superimposing the reference light with the totally back-scattered light.

20. The wave-front sensing device according to claim 17, wherein the evaluation device contains a simulation circuit processing light intensities sensed with sub-groups of detector elements according to a predetermined optical imaging function.

21. The wave-front sensing device according to claim 17, wherein the simulation circuit is arranged for simulating a Shack-Hartmann-Array of lenses by a Fourier transformation of the light intensities sensed with the sub-groups of detector elements.

22. The wave-front sensing device according to claim 17, wherein the sample light path contains a Shack-Hartmann-Array of lenses.

23. The wave-front sensing device according to claim 17, wherein the evaluation device is adapted to approximate the wave-front of the coherence-gated light by a set of orthogonal polynomials.

24. An imaging device for microscopic imaging a specimen, said imaging device comprising:

a wave-front sensing device according to claim 17; and a wave-front corrector device arranged in the sample light path;

wherein the wave-front corrector device generates adapted illumination light based on the aberration measurement.

25. The imaging device according to claim 24, wherein the wave-front corrector device comprises a deformable mirror or a liquid crystal spatial light modulator.

26. The imaging device according to claim 24, wherein the evaluation device includes a control circuit connected with the wave-front correcting device.

27. The imaging device according to claim 24, adapted to function as a confocal microscope or a multi-photon excitation microscope.

* * * * *